United States Patent
Thalgott et al.

(10) Patent No.: US 8,870,961 B2
(45) Date of Patent: Oct. 28, 2014

(54) SPINAL IMPLANT CONFIGURED FOR MIDLINE INSERTION

(75) Inventors: John S. Thalgott, Las Vegas, NV (US); David T. Stinson, Woodinville, WA (US); Anthony J. Fennell, Redditch (GB); John Parry, Stamford, CT (US); John J. Viscogliosi, New York, NY (US)

(73) Assignee: Centinal Spine, Inc., New York, NY (US)

( * ) Notice: Subject to any disclaimer, the term of this patent is extended or adjusted under 35 U.S.C. 154(b) by 70 days.

(21) Appl. No.: 12/941,190

(22) Filed: Nov. 8, 2010

(65) Prior Publication Data

US 2011/0166656 A1 Jul. 7, 2011

Related U.S. Application Data

(60) Provisional application No. 61/259,471, filed on Nov. 9, 2009.

(51) Int. Cl.
| | |
|---|---|
| *A61F 2/44* | (2006.01) |
| *A61F 2/30* | (2006.01) |
| *A61F 2/00* | (2006.01) |
| *A61F 2/28* | (2006.01) |
| *A61B 17/86* | (2006.01) |

(52) U.S. Cl.
CPC ..... *A61F 2/4455* (2013.01); *A61F 2002/30187* (2013.01); *A61F 2002/30794* (2013.01); *A61F 2002/30841* (2013.01); *A61F 2230/0034* (2013.01); *A61F 2002/0086* (2013.01); *A61F 2250/0032* (2013.01); *A61F 2002/30787* (2013.01); *A61F 2002/30892* (2013.01); *A61F 2310/00017* (2013.01); *A61F 2002/30497* (2013.01); *A61F 2002/30056* (2013.01); *A61F 2002/30617* (2013.01); *A61F 2002/2835* (2013.01); *A61F 2002/30062* (2013.01); *A61B 17/86* (2013.01); *A61F 2210/0004* (2013.01); *A61F 2230/0082* (2013.01); *A61F 2002/3008* (2013.01); *A61F 2220/0025* (2013.01); *A61F 2310/00131* (2013.01); *A61F 2250/0097* (2013.01); *A61F 2250/0098* (2013.01); *A61F 2002/30785* (2013.01); *A61F 2/4465* (2013.01); *A61F 2310/00023* (2013.01); *A61F 2002/3079* (2013.01); *A61F 2002/4475* (2013.01); *A61F 2002/3093* (2013.01); *A61F 2002/30266* (2013.01)
USPC .................. 623/17.16; 623/17.11

(58) Field of Classification Search
USPC ........................... 623/17.11, 17.16
See application file for complete search history.

(56) References Cited

U.S. PATENT DOCUMENTS 6,432,106 B1 * 8/2002 Fraser ................... 623/17.11
(Continued)

FOREIGN PATENT DOCUMENTS

| EP | 1972309 A1 | 9/2008 |
|---|---|---|
| GB | 2454229 A | 6/2009 |

(Continued)

*Primary Examiner* — Andrew Yang
(74) *Attorney, Agent, or Firm* — MH2 Technology Law Group, LLP (57) ABSTRACT

The embodiments provide a spinal implant that is configured for midline insertion into a patient's intervertebral disc space. The spinal implant may have a body and the body comprises one or more apertures. The apertures receive fixation elements, such as a screw and the like. The fixation element may comprise one or more anti-backout features, such as a split ring. In addition, at least some of the apertures are designed to permit a predetermined amount of nutation by a fixation element. The apertures that allow nutation enable the fixation element to toggle from one position to another, for example, during subsidence of the implant in situ. Some of the apertures may be configured to rigidly lock with the fixation elements. Moreover, the spinal implant may include features, such as one or more bores, that can accommodate imaging marks to help guide a surgeon.

11 Claims, 6 Drawing Sheets

(56) References Cited

U.S. PATENT DOCUMENTS

| | | | |
|---|---|---|---|
| 7,192,447 B2 * | 3/2007 | Rhoda ..................... | 623/17.11 |
| 2008/0183293 A1 | 7/2008 | Parry et al. | |
| 2009/0182430 A1 * | 7/2009 | Tyber et al. ............. | 623/17.16 |
| 2009/0192613 A1 | 7/2009 | Wing et al. | |
| 2009/0248163 A1 | 10/2009 | King et al. | |

FOREIGN PATENT DOCUMENTS

| | | |
|---|---|---|
| WO | 03/053290 A1 | 7/2003 |
| WO | 2008/102174 A2 | 8/2008 |

* cited by examiner

FIG. 1A

FIG. 1B
AMENDED

FIG. 2C
AMENDED

FIG. 2D
AMENDED

FIG. 4B ved alreadalready been inserted into the patient's spine, and as such, an implant introduction pathway may have to account for these prior existing conditions.

SPINAL IMPLANT CONFIGURED FOR MIDLINE INSERTION

CROSS-REFERENCE TO RELATED APPLICATIONS

This application claims priority to U.S. Provisional No. 61/259,471, filed Nov. 9, 2009, and entitled "SPINAL IMPLANT CONFIGURED FOR MIDLINE INSERTION," which is herein incorporated by reference in its entirety.

FIELD

The present disclosure relates to orthopedic implants, and more particularly, to spinal implants that facilitate fusion of bone segments and associated methods. Even more particularly, the disclosure relates to a spinal fusion implant configured for midline insertion.

BACKGROUND

The integrity of the spine, including its subcomponents like the vertebral bodies and intervertebral discs that are well known structural body parts forming the spine, are key to a patient's health. These parts may become crushed or damaged as a result of trauma or injury, or damaged by disease (e.g., by tumor, autoimmune disease) or as a result of wear over time or degeneration caused by the normal aging process.

In many instances, one or more damaged structural body parts can be repaired or replaced with a prosthesis or implant. For example, specific to the spine, one method of repair is to remove the damaged vertebra (in whole or in part) and/or the damaged disc (in whole or in part) and replace it with an implant or prosthesis. In some cases, it is necessary to stabilize a weakened or damaged spinal region by reducing or inhibiting mobility in the area to avoid further progression of the damage and/or to reduce or alleviate pain caused by the damage or injury. In other cases, it is desirable to join together the damaged vertebrae and/or induce healing of the vertebrae. Accordingly, an implant or prosthesis may be configured to facilitate fusion between two adjacent vertebrae. The implant or prosthesis may be placed without attachment means or fastened in position between adjacent structural body parts (e.g., adjacent vertebral bodies).

Typically, an implant or prosthesis is secured directly to a bone structure by mechanical or biological means. One manner of spine repair involves attaching a fusion implant or prosthesis to adjacent vertebral bodies using a fixation element, such as a screw. Most implants and their attachment means are configured to provide an immediate, rigid fixation of the implant to the implantation site. Unfortunately, after implantation the implants tend to subside, or settle, into the surrounding environment as the patient's weight is exerted upon the implant. In some cases, this subsidence may cause the rigidly fixed attachment means to either loosen, dislodge or potentially damage one or more of the vertebral bodies.

Several known surgical techniques can be used to implant a spinal prosthesis. The suitability of any particular technique may depend upon the amount of access available to the implant site. For instance, a surgeon may elect a particular entry pathway depending on the size of the patient or the condition of the patient's spine such as where a tumor, scar tissue, or other obstacle is present. Other times, it may be desirable to minimize intrusion into the patient's musculature and associated ligamentous tissue. In some patients who have had prior surgeries, implants or fixation elements may have already been inserted into the patient's spine, and as such, an implant introduction pathway may have to account for these prior existing conditions.

Thus, it is desirable to provide an implant that can be easily inserted in accordance with a specific pathway or approach. For example, in certain situations, it is desirable to provide a spinal implant that can be inserted using a midline approach. In addition, it is desirable to provide an implant and associated fixation elements that can account for subsidence that occurs with the implant subsequent to implantation while also providing rigid fixation.

Although the following discussion focuses on spinal implants or prostheses, it will be appreciated that many of the principles may equally be applied to other structural body parts within a human or animal body.

SUMMARY

The present disclosure describes a spinal implant that is configured for midline insertion into a patient's intervertebral disc space. In accordance with one exemplary embodiment, a spinal implant is provided having an upper surface, a lower surface, an anterior portion, a posterior portion and one or more apertures within the anterior portion for receiving at least one fixation element wherein the implant is configured for midline insertion. All or some of the apertures may be configured to permit a predetermined amount of nutation by a fixation element, thus allowing the fixation element to toggle from one position to another. The spinal implant may additionally include anti-migration features.

In another exemplary embodiment, a spinal implant comprises a body and one or more apertures. The body may comprise an upper surface, a lower surface, an anterior portion, and a posterior portion, wherein the body is configured for midline insertion between vertebral bodies of a patient's spine. The one or more apertures may be provided within the anterior portion of the body and can receive at least one fixation element. At least one of the apertures is configured to permit a predetermined amount of nutation by a fixation element.

In yet another exemplary embodiment, a method of treating a patient's spine comprises accessing at least a portion of a patient's spine via a posterior, midline approach. A spinal implant is then inserted between vertebral bodies of the patient's spine, wherein the spinal implant comprises a body having an upper surface, a lower surface, an anterior portion, a posterior portion, wherein the body is configured for midline insertion between vertebral bodies of a patient's spine, the implant further including one or more apertures within the anterior portion of the body for receiving at least one fixation element, and wherein at least one of the apertures is configured to permit a predetermined amount of nutation by a fixation element. The spinal implant is attached with the at least one fixation element to the vertebral bodies and a predetermined amount of toggling of the fixation element is permitted based on nutation of the fixation element during subsidence of the spinal implant.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1A:
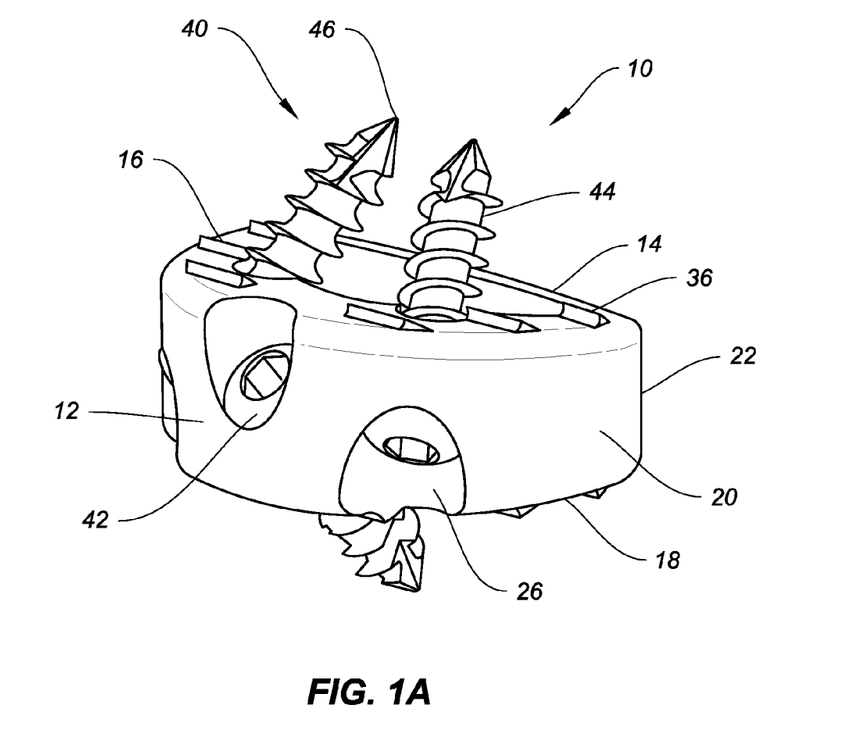
FIG. 1A illustrates a perspective view of a spinal implant of the present disclosure, with fixation screws.
Figure 1B:
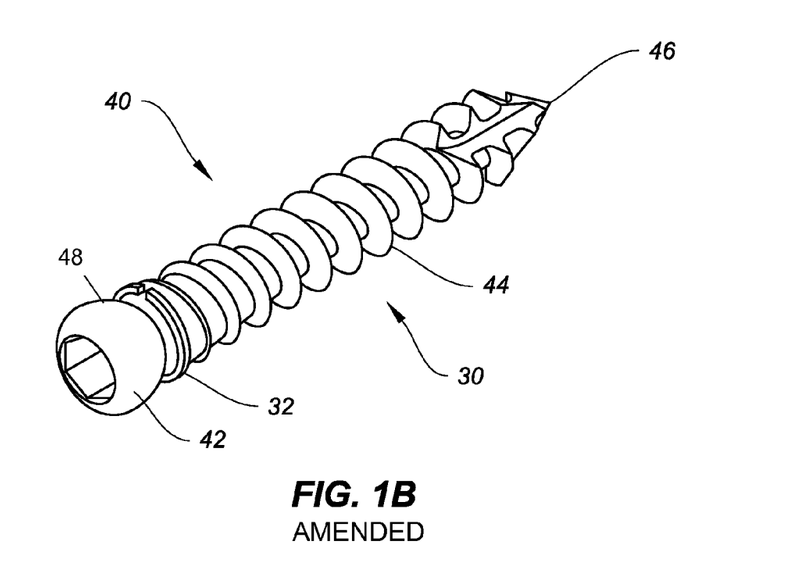
FIG. 1B illustrates a perspective view of an attachment system for the spinal implant of FIG. 1A.

Referring now to FIGS. 1A and 1B, a spinal implant 10 with an attachment system 30 of the present disclosure is shown. The spinal implant 10 may be employed in the lumbar or thoracic regions. Alternatively, the spinal implant 10 may be employed in the cervical region of the spine, in a manner similar to the one described for the cervical implant of U.S. patent application Ser. No. 11/938,476 filed Nov. 12, 2007, entitled "Orthopaedic Implants and Prostheses," which is herein incorporated by reference in its entirety. A cervical version may be provided so long as it is appropriately sized and configured, and the surgical approach takes into account this specific design.

The spinal implant 10 may include anterior and posterior portions 12, 14 and upper and lower surfaces 16, 18 profiled to correspond with the profile of any bone material to which they are to be secured. As shown, the upper and lower surfaces 16, 18 may further include surface enhancements, such as teeth 36, to enhance bone attachment, prevent migration and provide more stability. In one embodiment, the teeth 36 may be formed at about a 30 degree angle with respect to the upper or lower surfaces 16, 18 of the implant 10. In other embodiments, the teeth 36 can have an angle between about 25 to about 35 degrees. It is understood, however, that alternative surface modifications, such as surface roughenings, barbs, spikes, bumps, etc., may also be employed. Further, biological agents, such as bone growth factors may be employed to enhance bone attachment, either alone or in combination with the mechanical enhancements described above.

In one embodiment, the spinal implant 10 defines a generally wedge shaped structure suitable for a posterior midline insertion approach. As can be seen in FIGS. 2A-2D, the implant 10 may have an overall "D" shape. The anterior portion 12 extends into curved sidewalls 20 that intersect with proximal portion 14 at posterolateral corners 22. The posterolateral corners may be rounded, as shown, to provide overall smoothness to the implant profile and prevent undesirable damage to surrounding tissue. The spinal implant 10, however, may have other shapes depending on the desired implantation site. Furthermore, edges of the implant 10 may be shaped so as to cooperate with insertion tools to minimize unintended distraction of the vertebral bodies between which the implant 10 is being positioned during implantation.

The spinal implant 10 and its components may be formed of any suitable medical grade material, such as biocompatible metals like stainless steel, titanium, titanium alloys, etc. or a medical grade plastic, such as polyetheretherketone (PEEK) or another radiolucent material, ultra high molecular weight polyethylene (UHMWPE), etc. If so desired, the implant 10 may also be formed of a bioresorbable material. The bioresorbable material may be osteoconductive or osteoinductive (or both).

As shown, the spinal implant 10 may include a central opening or lumen 24 extending between the upper and lower surfaces 16, 18 to facilitate bony ingrowth or fusion between adjacent bone segments, such as vertebral bodies. If so desired, the opening 24 may be used to receive and hold bone graft material.

The spinal implant 10 may include holes 26 for placement of fixation screws therethrough to secure the spinal implant 10 to adjacent bone tissue. In the embodiment shown, the implant 10 includes three holes 26, such as one hole being centrally located (i.e., along the center line), and two laterally located (i.e., beside the center line.) Without compromising stability, the lateral holes 26 should be located in a manner that avoids the need to retract vessels during surgery. It has been postulated that extended retraction of vessels during surgery may lead to greater chances for complications to the patient. The lateral holes 26 should also be positioned so as to provide easier visibility of the surrounding implantation site for the surgeon.

Figure 2A:
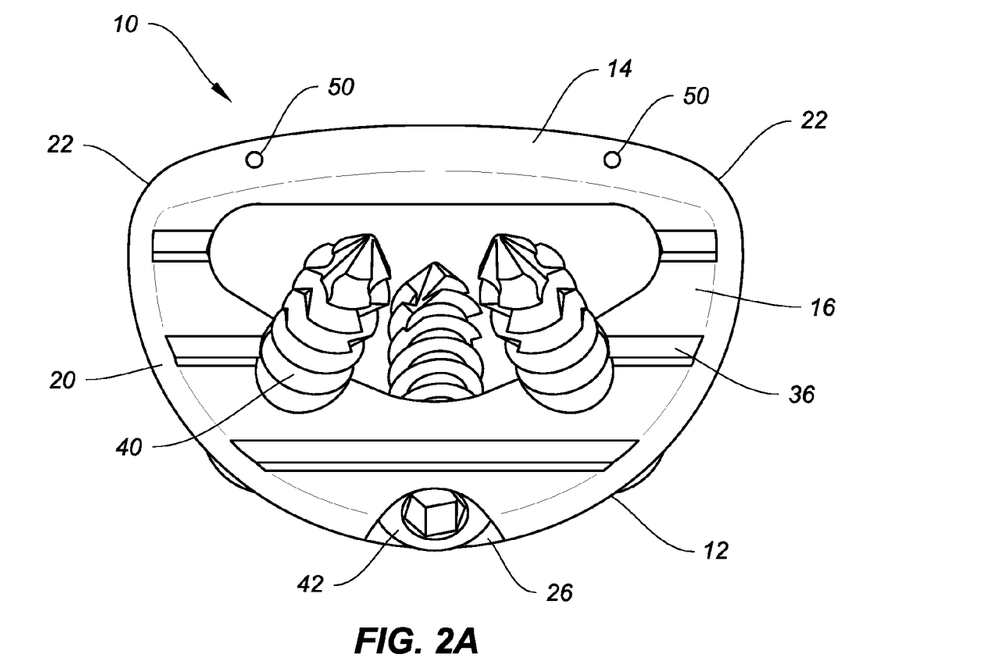
FIG. 2A illustrates a top-down view of the spinal implant and fixation screws of FIGS. 1A and 1B.
Figure 2B:
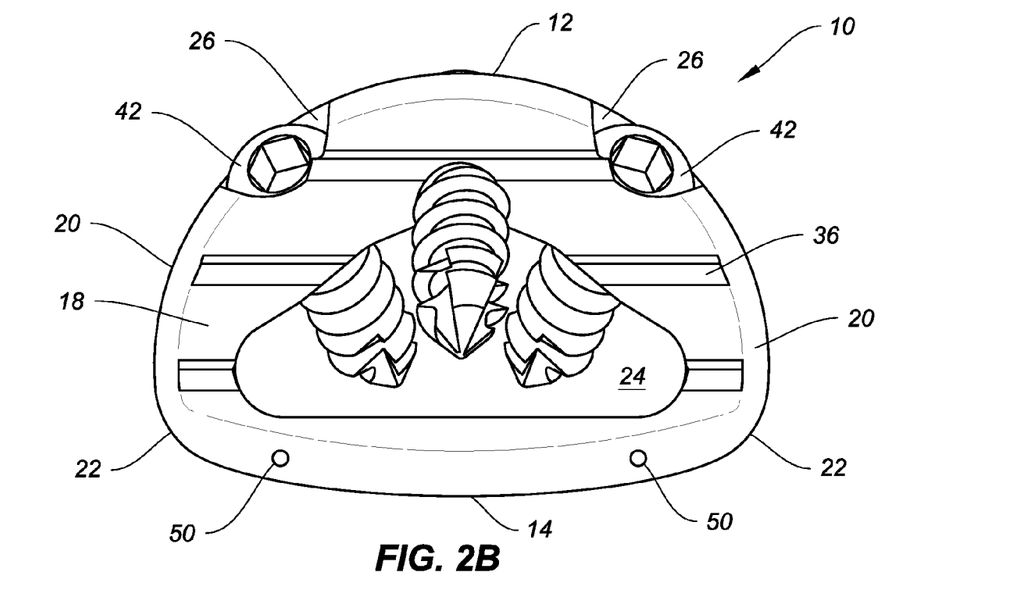
FIG. 2B illustrates a bottom-up view of the spinal implant and fixation screws of FIGS. 1A and 1B.
Figure 2C:
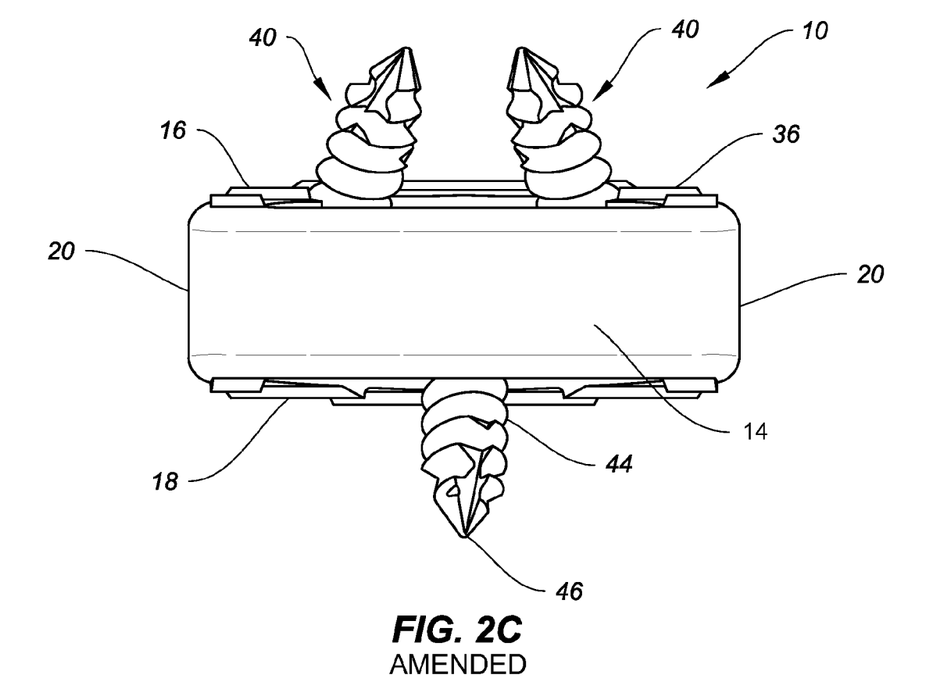
FIG. 2C illustrates a rear view of the spinal implant with fixation screws of FIGS. 1A and 1B.
Figure 2D:
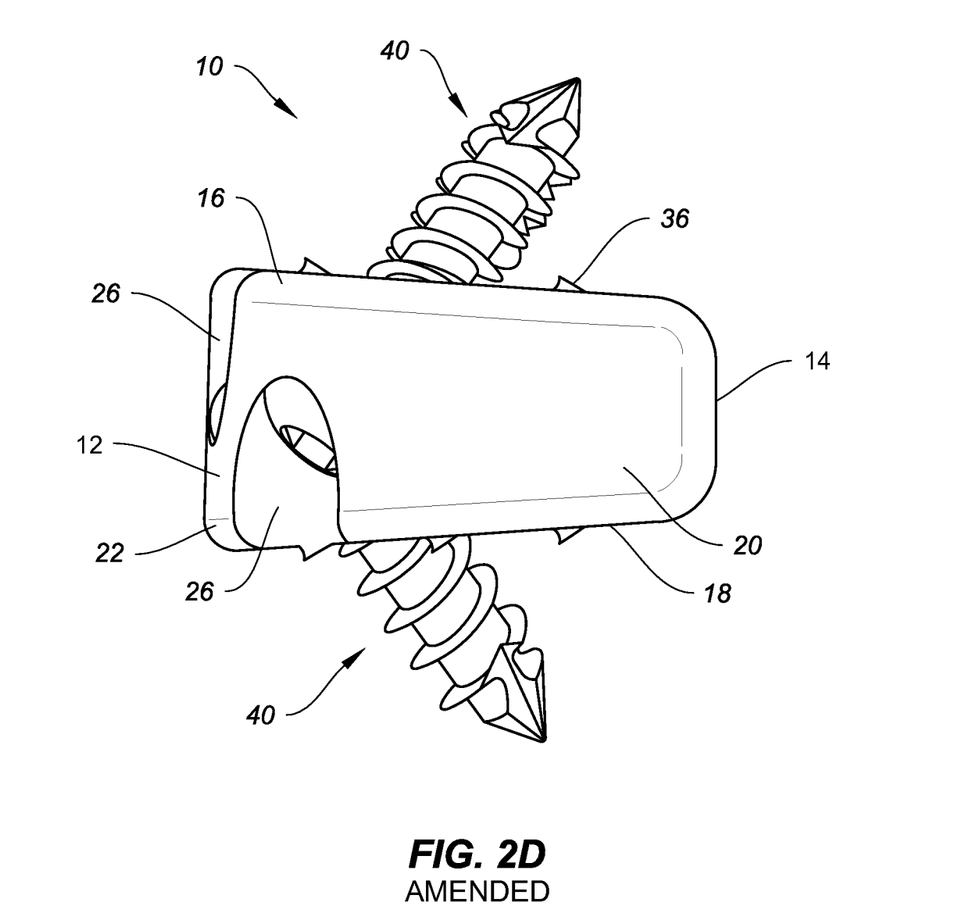
FIG. 2D illustrates a side view of the spinal implant with fixation screws of FIGS. 1A and 1B.
Figure 3A:
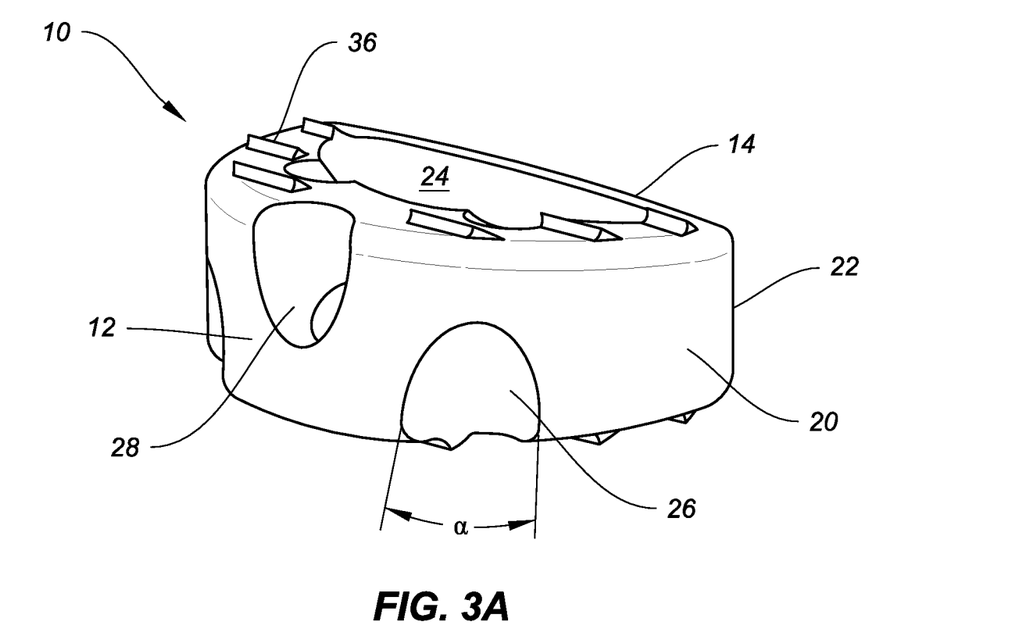
FIG. 3A illustrates another perspective view of the spinal implant of FIG. 1, without fixation screws.
Figure 3B:
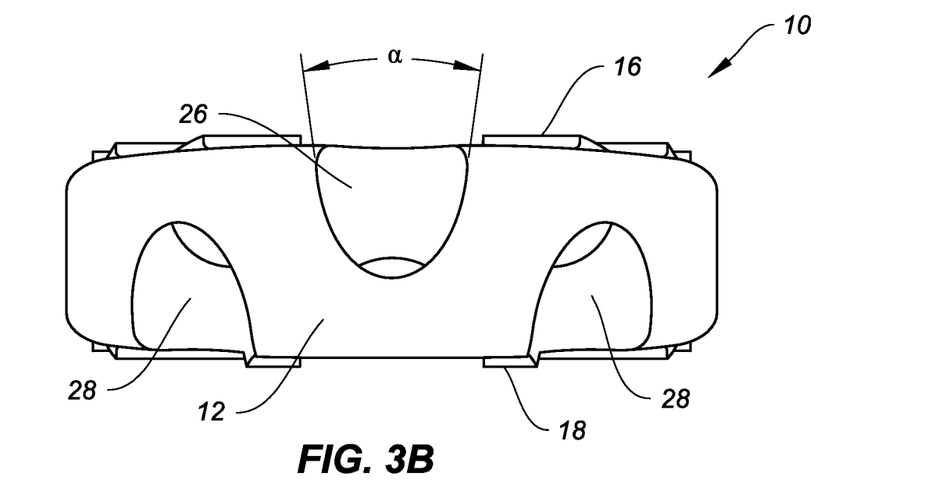
FIG. 3B illustrates a front view of the spinal implant of FIG. 3A.
Figure 4A:
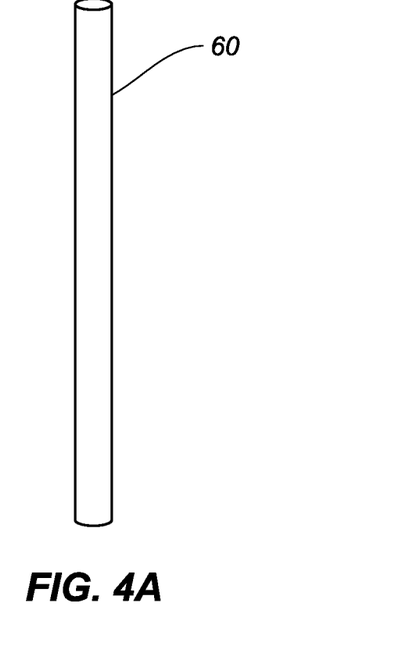
FIG. 4A illustrates a perspective view of an embodiment of an imaging marker of the present disclosure.
Figure 4B:
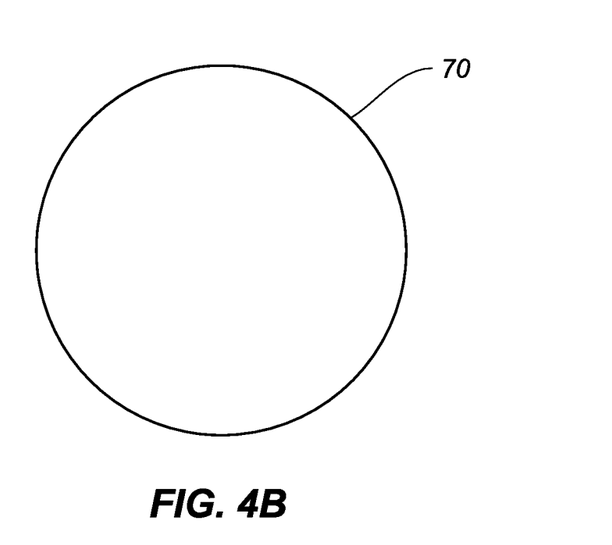
FIG. 4B illustrates a perspective view of another embodiment of an imaging marker of the present disclosure.

One skilled in the art will appreciate that the implant 10 may comprise any number of holes in any location on the implant 10. For instance, one embodiment of the spinal implant 10 may employ two of holes 26 that are located on either side of the center of implant 10. Optionally, the implant 10 may comprise other holes 26 for receiving features like a radiologic marker or other imaging marker. As shown in FIGS. 2A and 2B, the spinal implant 10 may include bores 50 near the posterolateral corners 22 for receiving an imaging marker 60. As illustrated in FIG. 4A, the imaging marker 60 may be formed of tantalum or a radiopaque material. The imaging marker 60 may be configured as a rod or other appropriate shape. An additional imaging marker 70 configured as a sphere or ball, as shown in FIG. 4B, may also be provided. Imaging marker 70 may be placed in a single counter bore, or hole 26, on the anterior side of the implant 10. These imaging markers 60, 70 can assist with placement of the implant 10 by providing visual cues for the surgeon intraoperatively.

The holes 26 provide a path through which securing means (e.g., fixation elements such as bone screws) may be inserted so as to secure the implant 10 to respective superior and inferior vertebral bodies (not shown). The holes 26 may be configured to accommodate a variety of securing mechanisms, such as screws, pins, staples, or any other suitable fastening device.

FIG. 1B illustrates an exemplary attachment system 30 of the present disclosure suitable for use with the spinal implant 10. The attachment system 30 may include a screw 40 and a split ring 32. The split ring 32 may be provided to prevent back-out of the screw 40. Other anti-back-out features may be incorporated into the embodiments of the present disclosure. In one embodiment, the fixation screws 40 may be self-tapping and/or self-drilling and may be of a bone screw-type, such as those well known to skilled artisans. In some embodiments, the head portion 42 of the fixation screws 40 extends into an elongate body 44 that terminates at a tip 46. While the implant 10 is shown with screws 40 sized and shaped for unicortical bone fixation, it is contemplated that bone screws sized and shaped for bicortical bone fixation may also be employed by embodiments of the present disclosure.

The holes 26 of the spinal implant 10 may be configured to permit a predetermined amount of screw toggle (i.e., angular skew) and enable a lag effect when the fixation screw 40 is inserted and resides inside the hole or lumen 26. In other words, the holes 26 may be designed to permit a certain degree of nutation by the screw 40, and thus, the screws 40 may toggle from one position to one or more different positions, for instance, during subsidence. It also is believed that the predetermined screw toggle (permitted by the clearance between the lumen, or hole 26 and the screw 40) promotes locking of the screw 40 to the implant 10 after subsidence subsequent to implantation. In one embodiment, the predetermined amount of screw toggle may be about 3 to 8 degrees, or about 5 to 6 degrees.

As shown, each of the holes 26 may have an opening with an angular range of α to accommodate for lordosis. The value of α may be about 7 to about 17 degrees. In some embodiments, the value of α may be about 8, 12, or 16 degrees, for example. As also shown, a contoured seat or countersink 28 may reside within holes 26. The underside 48 of the head 42 of screws 40 may be provided with a contour to allow it to move against the countersink 28 in a predetermined angular fashion. Alternatively, the holes 26 of implant 10 may be configured with little or no clearance to achieve rigid fixation, for example, when implant 10 is to be implanted into sclerotic bone.

In one exemplary method of inserting the spinal implant 10, the surgeon prepares the implantation site by removing some disc material from the disc space between two adjacent vertebrae. The spinal implant 10 may be provided to the surgeon with the screws 40 pre-attached, or separately, as desired. Using a posterior midline approach, the surgeon then places the implant 10 in the desired location of a patient's spine. Once in the correct location, the surgeon can tighten the screws 40 into the surrounding bone tissue, thereby securing the implant 10.

As noted, the implant 10 may be configured to permit a predetermined amount of screw toggle and enable a lag effect when the fixation screw 40 is inserted and resides inside the hole or lumen 26. Upon tightening, the lag effect may be observed whereby the implant 10 draws bone tissue towards itself, which may promote better fusion.

As further noted, the predetermined screw toggle promotes locking of the screw 40 to the implant 10 after subsidence subsequent to implantation. For example, after surgery, the patient's natural movement will result in settling and subsidence of bone tissue and the implant 10 in situ. It is believed that during this process, the weight exerted upon the implant 10 causes the fixation screws 40 to toggle and consequently lock against one or more surfaces of the holes 26 of the implant 10.

Some practitioners prefer to allow some degree of movement between the implant and the adjacent vertebral body after implantation. In that case the screw heads 42 may be provided with contours on its underside 48 as previously discussed that allow the screws 40 to nutate and toggle with respect to the contoured seat 28 of the implant 10. Other practitioners may prefer a more rigid implant that is firmly locked to the adjacent vertebral body. The embodiments of implant 10 allow either preference.

In a rigidly fixed version, the screws 40 may be provided without the contour on its underside 48 (i.e., a relatively flat underside) while the opening 26 of the implant 10 would likewise not include a contoured seat or countersink 28. Thus, when secured together, the screws 40 and implant 10 may form a rigidly locked construct. Where rigid fixation is desired (i.e., no toggle), the underside of the screws 40 may also include surfaces features as well in order to provide secure attachment to the implant 10.

While a toggle and a rigidly fixed version of the implant 10 and screws 40 are described, it is understood that a combination of toggling and rigid fixation may be accomplished in a single implant 10 and attachment system 30. For example, it is possible to provide an implant 10 that allows toggling of one or more screws 40, while also allowing rigid fixation of the other of the screws 40.

It will also be appreciated that the angular positioning of the various holes, as described above, allows the present implant 10 to be of a relatively small size and therefore insertable from a midline approach within the intervertebral spaces of the spine. Thus, it will be appreciated that the angular positioning of the holes can assist effective operation of the implant 10 and the ability to "stack" implants in adjacent multilevel procedures without the securing means interfering with each other. Such a feature can be of major significance in some situations and applications.

As further noted, the predetermined screw toggle promotes locking of the screw 40 to the implant 10 after subsidence subsequent to implantation. For example, after surgery, the patient's natural movement will result in settling and subsidence of bone tissue and the implant 10 in situ. It is believed that during this process, the weight exerted upon the implant 10 causes the fixation screws 40 to nutate and/or toggle and eventually lock against one or more surfaces of the holes 26 of the implant 10.

Other embodiments of the disclosure will be apparent to those skilled in the art from consideration of the specification and practice of the disclosure provided herein. It is intended that the specification and examples be considered as exemplary only.

What is claimed is:

1. A spinal implant comprising:
   a body having an upper surface, a lower surface, an anterior portion, a posterior portion, curved sidewalls, and a central opening extending between the upper and lower surfaces, the curved sidewalls intersecting with the proximal portion at rounded posterolateral corners with the body being widest between the posterolateral corners, the curved sidewalls and anterior portion together forming a rounded, convex curvature such that the body has an overall D-shape for midline insertion between vertebral bodies of a patient's spine; and
   one or more apertures within the anterior portion of the body for receiving at least one fixation element, the one or more apertures comprising a first aperture centrally located at the anterior portion and a pair of second apertures laterally located at the anterior portion, each of the apertures having a countersink therein and an opening with an angular range of about 7 to about 17 degrees;
   wherein the apertures are configured to permit a predetermined amount of nutation by the fixation elements.

2. The spinal implant of claim 1 further comprising one or more bores for receiving an imaging marker.

3. The spinal implant of claim 1 further comprising one or more bores for receiving a rod-shaped imaging marker.

4. The spinal implant of claim 1 further comprising one or more bores for receiving a ball-shaped imaging marker.

5. The spinal implant of claim 1, wherein at least one of the apertures is configured to permit about 5 degrees of nutation by the fixation element.

6. The spinal implant of claim 1, wherein the first aperture is configured to permit about 5 degrees of nutation by the fixation element.

7. The spinal implant of claim 1, wherein the second aperture is configured to permit about 5 degrees of nutation by the fixation element.

8. A method of treating a patient's spine comprising:

accessing at least a portion of a patient's spine via a posterior, midline approach;

inserting a spinal implant between vertebral bodies of the patient's spine, wherein the spinal implant comprises a body having an upper surface, a lower surface, an anterior portion, a posterior portion, curved sidewalls, and a central opening extending between the upper and lower surfaces, the curved sidewalls intersecting with the proximal portion at rounded posterolateral corners with the body being widest between the posterolateral corners, the curved sidewalls and anterior portion together forming a rounded, convex curvature such that the body has an overall D-shape for midline insertion between vertebral bodies of a patient's spine, the implant further including one or more apertures within the anterior portion of the body for receiving at least one fixation element, the one or more apertures comprising a first aperture centrally located at the anterior portion and a pair of second apertures laterally located at the anterior portion, each of the apertures having a countersink therein and an opening with an angular range of about 7 to about 17 degrees; wherein the apertures are configured to permit a predetermined amount of nutation by the fixation elements; and attaching the spinal implant with the at least one fixation element to the vertebral bodies.

9. The method of claim 8, wherein the spinal implant comprises one or more bores for receiving an imaging marker and positioning the spinal implant based on visual cues provided by the imaging marker.

10. The method of claim 9, wherein inserting the spinal implant comprises positioning the spinal implant based on visual cues provided by a radiopaque imaging marker on an intraoperative image.

11. The spinal implant of claim 1, further including teeth on the upper or lower surfaces of the body.

* * * * *